(12) United States Patent
Schaff et al.

(10) Patent No.: US 10,024,849 B2
(45) Date of Patent: Jul. 17, 2018

(54) SYSTEMS, DEVICES, AND METHODS FOR AGGLUTINATION ASSAYS USING SEDIMENTATION

(71) Applicant: National Technology & Engineering Solutions of Sandia, LLC, Albuquerque, NM (US)

(72) Inventors: Ulrich Y. Schaff, Livermore, CA (US); Gregory Jon Sommer, Livermore, CA (US); Anup K. Singh, Danville, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 417 days.

(21) Appl. No.: 14/853,660

(22) Filed: Sep. 14, 2015

(65) Prior Publication Data
US 2016/0061829 A1    Mar. 3, 2016

Related U.S. Application Data

(62) Division of application No. 13/423,073, filed on Mar. 16, 2012, now Pat. No. 9,244,065.

(51) Int. Cl.
*G01N 33/543* (2006.01)
*G01N 33/537* (2006.01)
(Continued)

(52) U.S. Cl.
CPC ..... *G01N 33/54366* (2013.01); *B01D 21/262* (2013.01); *B01L 3/5021* (2013.01); *B01L 3/50215* (2013.01); *B01L 3/502715* (2013.01); *B01L 3/502738* (2013.01); *B01L 3/502753* (2013.01); *G01N 33/537* (2013.01); *G01N 33/538* (2013.01); *G01N 33/543* (2013.01); *G01N 33/54313* (2013.01); *B01L 3/502761* (2013.01); *B01L 2200/0631* (2013.01); *B01L 2200/0647* (2013.01); *B01L 2200/10* (2013.01); *B01L 2300/0627* (2013.01); *B01L 2300/0803* (2013.01); *B01L 2300/0861* (2013.01);
(Continued)

(58) Field of Classification Search
None
See application file for complete search history.

(56) References Cited

U.S. PATENT DOCUMENTS

| | | | |
|---|---|---|---|
| 3,744,974 A | 7/1973 | Maddox et al. | |
| 5,639,428 A | 6/1997 | Cottingham | |

(Continued)

OTHER PUBLICATIONS

PubChem Search results for "2,3-dihydroxypropyl octanoate". Retrieved on Oct. 5, 2016 from the internet: https://www.ncbi.nim.nih.gov/pccompound/?term=2%2C3-dihydroxypropyl+octanoate. (4 pp.).

(Continued)

*Primary Examiner* — Erik B Crawford
(74) *Attorney, Agent, or Firm* — Madelynne J. Farber

(57) ABSTRACT

Embodiments of the present invention include methods for conducting agglutination assays using sedimentation. Aggregates may be exposed to sedimentation forces and travel through a density medium to a detection area. Microfluidic devices, such as microfluidic disks, are described for conducting the agglutination assays, as are systems for conducting the assays.

6 Claims, 6 Drawing Sheets

(51) Int. Cl.
  *B01D 21/26* (2006.01)
  *B01L 3/00* (2006.01)
  *G01N 33/538* (2006.01)

(52) U.S. Cl.
  CPC ............... *B01L 2400/0409* (2013.01); *B01L 2400/0457* (2013.01)

(56) References Cited

U.S. PATENT DOCUMENTS

| | | | |
|---|---|---|---|
| 5,892,577 A | 4/1999 | Gordon | |
| 6,319,469 B1* | 11/2001 | Mian | B01F 13/0059 422/63 |
| 7,332,326 B1 | 2/2008 | Kellogg et al. | |
| 2002/0106786 A1 | 8/2002 | Carvalho et al. | |
| 2002/0151043 A1* | 10/2002 | Gordon | B01L 3/5027 435/287.2 |
| 2004/0072278 A1 | 4/2004 | Chou et al. | |
| 2005/0186685 A1 | 8/2005 | Kange et al. | |
| 2011/0045958 A1 | 2/2011 | Pedrazzini | |
| 2013/0260447 A1 | 10/2013 | Link | |
| 2014/0273241 A1 | 9/2014 | Ochranek et al. | |

OTHER PUBLICATIONS

PubChem entry for TWEEN 20. Retrieved on Oct. 4, 2016 from the internet: https://pubchem.ncbi.nlm.nih.gov/compound/Tween_20#section=Names-and-identifiers. (2 pp.).

Sigma-Aldrich product page For TWEEN 20 archived from Jun. 28, 2012. Retrieved on Oct. 5, 2016 from the internet: https://web.archive.org/web/20120628080753/http://www.sigmaaldrich.com/catalog.product/sial/p1379?lang=en&region=. (43 pp.).

Buck et al., "Design Strategies and Performance of Custom DNA Sequencing Primers," BioTechniques 1999; 27:528-536.

Suzuki et al., "Experimental optimization of probe length to increase the sequence specificity of high-density oligonucleotide microarrays," BMC Genomics 2007; 8:373.

Gusev et al., "Capillary columns with in situ formed porous monolithic packing for micro high-performance liquid chromatography and capillary electrochromatography", Journal of Chromatography A, 1999, vol. 855(1), pp. 273-290.

Huang et al., "The primary structure of *Staphylococcal enterotoxin* B: III. The cyanogen bromide peptides of reduced and aminoethylated enterotoxin B, and the complete amino acid sequence", Journal of Biological Chemistry, 1970, vol. 245(14), pp. 3518-3525.

IVD Technology, "Microfluidic applications for IVDs", DX Directions, 2010, Spring, pp. 1-26.

Kim et al., "Fully integrated lab-on-a-disc for nucleic acid analysis of food-borne pathogens", Analytical Chemistry, 2014, vol. 86, pp. 3841-3848.

Koh et al., "Centrifugal microfluidic platform for ultrasensitive detection of botulinum toxin", Analytical Chemistry, 2015, vol. 81, pp. 922-928.

Churchill et al., "Detection of Listeria monocytogenes and the toxin listeriolysin O in food", Journal of Microbiological Methods, 2006; 64:141-170.

* cited by examiner

SYSTEMS, DEVICES, AND METHODS FOR AGGLUTINATION ASSAYS USING SEDIMENTATION

CROSS-REFERENCE TO RELATED APPLICATION(S)

This application is a divisional application of, and discloses subject matter that is related to subject matters disclosed in, co-pending parent application U.S. Ser. No. 13/423,073, filed Mar. 16, 2012 and entitled "SYSTEMS, DEVICES, and METHODS FOR AGGLUTINATION ASSAYS USING SEDIMENTATION". The present application claims the priority of the aforementioned application which is hereby incorporated by reference, in its entirety, for any purpose.

STATEMENT REGARDING RESEARCH & DEVELOPMENT

Described examples were made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

Embodiments of the invention relate generally to agglutination assays utilizing sedimentation forces, and include embodiments utilizing disk-based microfluidics.

BACKGROUND

Agglutination assays may be used to detect the presence of or measure an amount of an analyte in a sample. Typical applications include testing blood serum for the presence of reactive antibodies to known pathogens or testing blood antigen type for donor compatibility. Analytes present in the sample cause particles (e.g. beads) in the sample to interact with each other to form clumps (also called agglutinate or aggregates). Agglutination assays are typically conducted by adding a sample of interest to a suspension of antibody- or antigen-coated particles deposited on a card, and rocking the card manually for a few minutes to facilitate agglutination (clumping). Specific interaction between the antibody/antigen with substances of interest in the sample causes visible aggregation of the particles which serves as the assay readout.

Therefore, a typical agglutination assay is only able to report whether analyte concentration in a sample is above or below a given threshold value (e.g. there are visible clumps of agglutinate or there are not). Furthermore, manual mixing of assay particles and sample by rocking a card can result in a considerable variability of assay conditions yielding a large uncertainty range in the threshold value. Therefore, agglutination assays are typically performed only for applications where the analyte is either present in large quantities in the sample or otherwise almost entirely absent.

DETAILED DESCRIPTION

Figure 1:
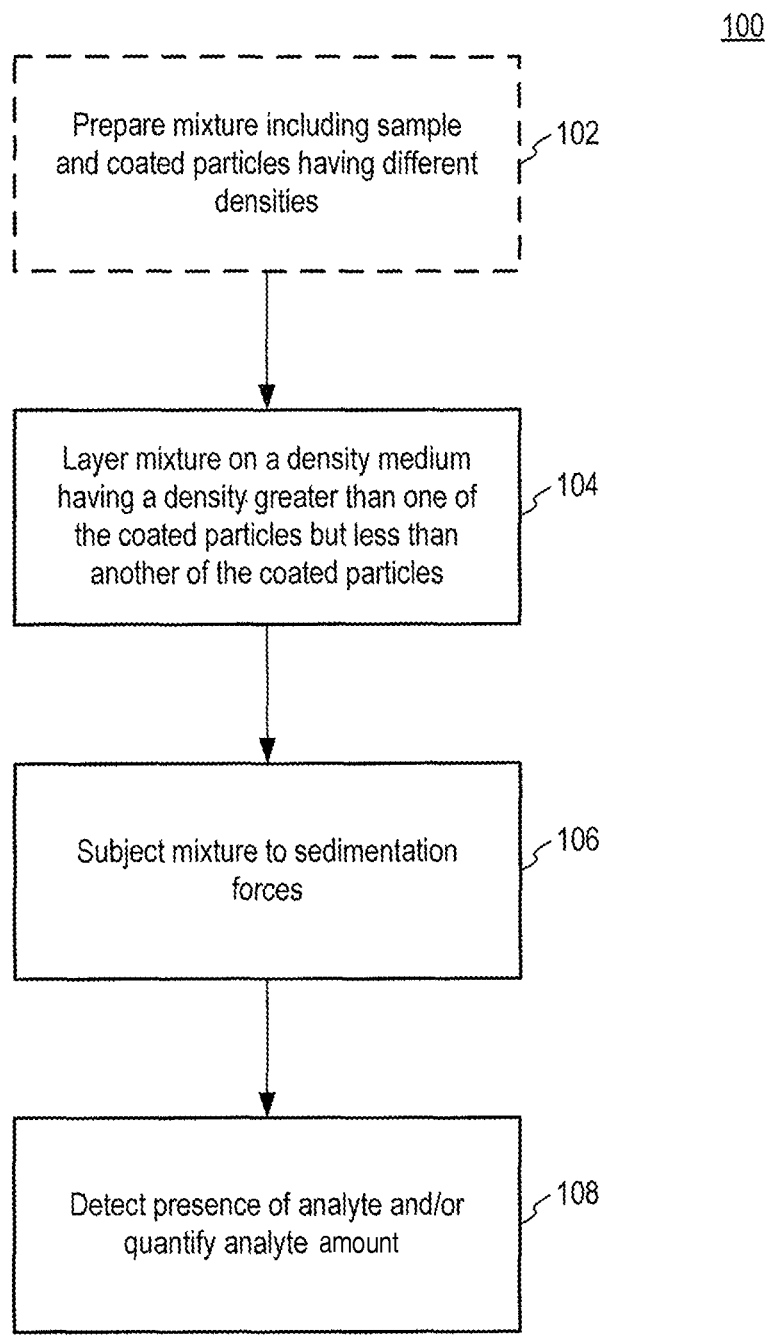
FIG. 1 is a flowchart of an example of a method for conducting an agglutination assay in accordance with embodiments of the present invention.

Certain details are set forth below to provide a sufficient understanding of embodiments of the invention. However, it will be clear to one skilled in the art that embodiments of the invention may be practiced without various of these particular details or with additional details. In some instances, well-known microfluidic device components, processing techniques, detection sensors and systems components, circuits, control signals, timing protocols, and software operations have not been shown in detail in order to avoid unnecessarily obscuring the described embodiments of the invention.

As described above, agglutination assays are typically only used where the analyte is either present in large quantities in a sample or otherwise almost entirely absent, due to the challenges in conducting a reliable, sensitive agglutination assay. For applications requiring higher sensitivity and more precise knowledge of analyte concentration, it may be necessary to detect and quantify microscopic aggregates within the assay particle suspension (e.g. not reliably visible aggregates). Several methods for quantifying agglutination assays have been developed including measuring changes in light scattering caused by formation of microaggregates. However, these methods tend to increase required sample and reagent volumes or introduce complex instrumentation rendering them less useful for low cost assays.

Embodiments of the present invention include agglutination assays utilizing sedimentation. As will be described further below, example agglutination assays may provide improved detection and/or quantification of analyte present in a sample. The improved detection and/or quantification may be due in part to the manner in which the assay is conducted, and/or the device or system used to conduct the agglutination assay. Although improvement is described relative to typical assays, the advantages or improvements achieved by examples of the present invention are provided herein to aid in the understanding of the disclosure, and it is to be understood that not all embodiments of the present invention may provide all, or any, of the improvements or advantages described herein.

Agglutination assays utilizing sedimentation described herein may be used to detect and/or quantify an analyte in a sample. Any of a variety of suitable samples may be used including, but not limited to, whole blood, buffer solutions, or other biological fluid samples. The biological fluid may be combined with buffer or other fluids to form the sample. Generally, the sample may include analytes of interest to be detected and/or quantified in accordance with embodiments of the present invention.

Analytes of interest may include chemicals and/or molecules that are of interest for detection in a sample. Any of a variety of analytes of interest may be detected in accordance with embodiments of the present invention, including proteins, RNA, and/or DNA.

Agglutination assays in accordance with embodiments of the present invention may occur in part using sedimentation. Sedimentation generally refers to the process of movement of a particle or substance under an influence of a gravitational field. Sedimentation forces may be generated due to gravity or centrifugal forces, for example.

Examples of agglutination assays described herein may be used to detect the presence of an analyte of interest. Accordingly, a detection signal received from appropriate detection area may indicate the presence of the analyte of interest in the sample, as will be described further below. In some examples, the detection signal may be required to be above a threshold value to indicate presence of the analyte of interest in the sample to avoid possible false positives should some detection signal be received from the detection area due to other factors unrelated to the assay.

Examples of agglutination assays described herein may be used to quantify an amount of analyte of interest present in a sample. A magnitude or strength of a detection signal from an appropriate detection area may be indicative of the amount of analyte present in the sample.

Examples of agglutination assays utilizing sedimentation described herein may utilize coated particles. Any particles suitable for conducting agglutination assays may be used, including but not limited to, beads such as polystyrene beads or silica beads. Substantially any bead radii may be used. Examples of beads may include beads having a radius ranging from 150 nanometers to 10 microns. Other sizes may also be used.

The particles (e.g. beads) may be coated with affinity reagents. The affinity reagent may be any suitable reagent for binding to an analyte of interest. Suitable reagents include antibodies for binding to one or more proteins, antigens, and DNA probes for binding to DNA and/or mRNA in a fluid sample. To facilitate agglutination assays, the affinity reagents may be able to recognize multiple sites on the analyte of interest. In this manner, multiple particles may bind to a single analyte of interest at different locations, facilitating aggregate formation. Examples of affinity reagents able to recognize multiple sites on the analyte of interest include polyclonal antibodies, antigens with multiple potential binding sites, mixtures of monoclonal antibodies with different recognition sites, and mixtures of nucleotide probes with different hybridization sites. The affinity reagents may be coated on the particles in generally any suitable matter. In some examples, beads may be commercially available coated with appropriate affinity reagents.

Some of the particles may be labeled with a label (e.g. a tag) suitable for detection. Fluorescent tags (e.g. fluorophores) may provide an optical detection signal, however colorimetric or radioactive tags may also be used. In some examples, the particle itself may serve as the label, e.g. fluorescent beads.

Examples of agglutination assays utilizing sedimentation described herein may utilize density media. Density medium (also referred to as density media herein) is generally a liquid which may have a density selected based on the sample or coated particles, as described further herein. The density media may generally be implemented using a fluid having the selected density. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in a salt solution. More generally, viscosity and density may be adjusted by changing a composition of the media. Varying the concentration of solutes such as, but not limited to, sucrose or dextran, in the density media, may adjust the density and/or viscosity of the media. In some embodiments, the density media may include a detergent, such as Tween 20. The detergent may enhance a wash function of transport through the density media.

FIG. 1 is a flowchart of an example of a method for conducting an agglutination assay in accordance with embodiments of the present invention. In block 102, a mixture may be prepared including the sample and coated particles having different densities. Block 102 may be optional in some examples. In block 104, the mixture may be layered on a density medium having a density greater than one of the coated particles and smaller than another of the coated particles. Agglutination may occur, if suitable analytes are present in the sample, to form aggregates of analyte in the sample and particles in the mixture. In block 106, the mixture may be subject to sedimentation forces. If aggregates are present, they may sediment through the density medium to a detection area. If aggregates are not present, the particles having a density less than the density medium may remain layered on the density medium and may not sediment through the density medium. In some examples, the particles having a density less than the density medium may be labeled for detection. Accordingly, if the particles having a density less than the density medium are not sedimented through to the detection area, no analyte may later be detected. In block 108, the presence of the analyte may be detected in the detection area and/or quantified. In this manner, aggregates too small to be detected visually may also be collected at the detection are and contribute to the detection and/or quantification of the analyte of interest. It is to be understood that additional blocks may be present in some examples. Moreover, aggregates may be formed at any time during the method.

Figure 2:
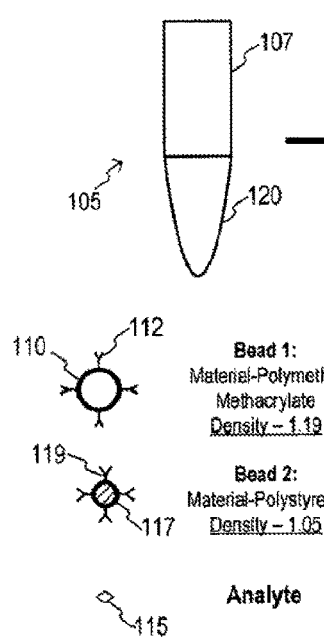
FIGS. 2A, 2B, and 2C are schematic illustrations of different stages of agglutination assays in accordance with embodiments of the present invention.
Figure 2:
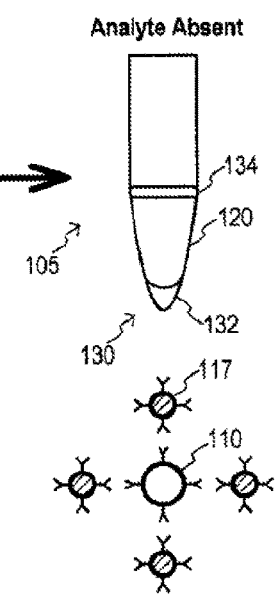
Figure 2:
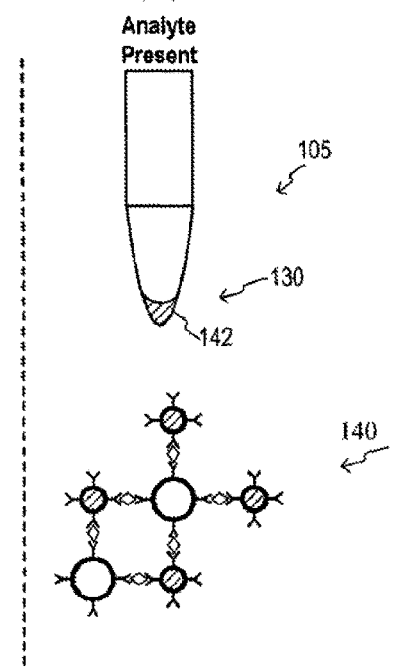

Example methods arranged in accordance with the flowchart shown in FIG. 1 are further described with reference to FIGS. 2A-2C. FIGS. 2A-2C are schematic illustrations of different stages of agglutination assays in accordance with embodiments of the present invention. The embodiments of the present invention represented in FIGS. 2A-2C may occur during performance of a method according to FIG. 1, e.g. utilize a density-based mechanism for conducting an agglutination assay.

Recall in block 102 of FIG. 1, a mixture may be prepared including a sample and coated particles having different densities. The sample may or may not include the analyte of interest. Generally, one population of particles may be included in the mixture that may have a density greater than the density medium used in the assay, and another population of particles may be included in the mixture that may have a density less than the a density of the density medium used in the assay. The mixture may be prepared by mixing the particles with the sample, by introducing the sample into a mixture already containing one or both population of particles, or through other combinations. In some examples, the mixture is already provided.

FIG. 2A illustrates the mixture 107 contained in a device 105. The device 105 may, for example, be implemented as a vial or a microfluidic device, as will be described further below. The mixture 107 includes a sample and coated particles (e.g. beads) having different densities. The example of FIG. 2A illustrates two bead populations. A first bead population may include the bead 110, shown schematically in FIG. 2A below the schematic depiction of the device 105. The bead 110 may have a density greater than the density media. In the example of FIG. 2A, the bead 110 may be implemented as a polymethyl methacrylate bead having a density of approximately 1.19 g/cm$^3$ and diameter of 1 μm. The bead 110 may be coated with affinity reagents, including the affinity reagent 112, which may be selected to bind with a particular analyte of interest. An analyte of interest 115 is also shown schematically in FIG. 2A.

A second bead population may include the bead 117. The bead 117 may have a density less than a density of the density media. In the example of FIG. 2A, the bead 117 may be implemented as a fluorescent polystyrene bead having a density of approximately 1.05 g/cm$^3$ and diameter of 1 μm. The bead 117 may be coated with affinity reagents, including the affinity reagent 119, which may be selected to bind with the particular analyte of interest in such a way as to form an agglutinate with the bead 110 and the analyte 115. The second population of beads having a density less than that of the density media, including the bead 117, may also be labeled with a detection label. As described above, the detection label may include a fluorescent label, chemical label, electronic label, or combinations thereof. As will be described further, detection of the detection label in a detection area may be indicative of the presence of the analyte of interest. Accordingly, embodiments of the invention include providing a mixture of low density labeled beads and high density unlabeled beads.

Accordingly, FIG. 2A illustrates a mixture 107 which may include a sample, and coated particles including bead 110 and bead 117. The sample may include the analyte of interest 115 or may not. The amount of bead populations provided in the mixture may vary. Generally, sufficient amounts of each bead population are provided to generate aggregates for the expected amount of analyte in the sample.

Referring back to FIG. 1, in block 104, the mixture may be layered on a density medium having a density greater than one of the coated particles but less than another of the coated particles. As described with reference to FIG. 2A, the mixture may include a first population of particles having approximately one density greater than a density of the density media and a second population of particles having approximately another density less than the density of the density media. The mixture may be layered on the density medium by providing the mixture in fluid communication with the density medium such that aggregates may pass through the density medium responsive to sedimentation forces. For example, the mixture may be loaded into a device such that the mixture is next to the density medium, on top of the density medium, or separated from the density medium by other fluids or device components.

Referring to FIG. 2A, the mixture 107 is loaded into the device 105 such that it is adjacent the density media 120. For example, if the device 105 is implemented as a vial, the mixture 107 may be pipetted or otherwise dispensed on top of the density media 120. If the device 105 is implemented as a microfluidic device, the mixture 107 may be introduced to the device next to the density media 120. In other examples, fluids or device features may separate the density media 120 and the mixture 107, however, the aggregates may travel across those intervening fluids or features to allow sedimentation of aggregates.

Following block 104 of FIG. 1, in some examples, an incubation period may be provided to allow aggregates to form. In other examples, aggregates may have already formed in the mixture during introduction to a device or prior to introduction to the device. In other examples, aggregates form or continue to form following further blocks of the method. As described above, aggregates may form when the analyte of interest is present in the sample and may not form if the analyte of interest is not present.

Referring back to FIG. 1, in block 106, the mixture may be subjected to sedimentation forces. In some examples, the mixture may be subjected to sedimentation forces using gravity. In other examples, the mixture may be subjected to sedimentation forces using centrifugal forces. Referring to FIG. 2A, in examples where the device 105 is a vial, the vial may be left to incubate in a gravitational field, allowing sedimentation of aggregates, if present, in the mixture 107. Alternatively, the vial may be placed in a centrifuge and the centrifuge spun to allow sedimentation of the aggregates, if present, in the mixture 107.

FIG. 2B is a schematic illustration of the device 105 following exposure to sedimentation forces when no aggregate has formed in the mixture, which may be an indication that no analyte of interest is present in the sample. The lack of aggregate formation is indicated schematically below the device 105 in FIG. 2B. The bead populations, including bead 110 and 117, have not formed aggregates by binding with target analyte, since no analyte or insufficient analyte, is present in the sample. Accordingly, these bead populations remain unbound in the mixture. Following exposure to sedimentation forces, the particles (e.g. beads) having a density greater than the density medium may sediment through the density medium to a detection area 130. Accordingly, the bead population 132, including the bead 110 for example, may be found in the detection area 130 following sedimentation. However the particle (e.g. bead) population that is less dense than the density medium may not travel through the density medium responsive to the sedimentation forces, and following sedimentation the bead population 134, including the bead 117 for example, may not be found at the detection area and may instead be located, for example, above or adjacent to the density medium 120, as shown in FIG. 2B. Recall that the bead population 134, which includes beads that are less dense than the density medium, may include the detection label. Accordingly, the detection label in the example of FIG. 2B may not be found at the detection area 130, and may not contribute to a detection signal measured at the detection area 130.

FIG. 2C is a schematic illustration of the device 105 following exposure to sedimentation forces when aggregate has formed in the mixture, which may be an indication that analyte of interest is present in the sample. The aggregate formation is indicated schematically below the device 105 in FIG. 2C. The bead populations, including bead 110 and 117, may form aggregates, including the aggregate 140. The aggregates are formed in part because the analytes of interest bind to both the bead populations. The analytes of interest, as generally described above, may bind to the bead populations of interest at respective different sites of the analyte. Accordingly, the analyte 115 of FIG. 2C is shown bound to the beads 110 and 117. The aggregates, including the aggregate 140, will be denser than the density media and will accordingly travel through the density media responsive to the sedimentation forces. Accordingly, following sedimentation, aggregates, including the aggregate 140 may be present in a pellet 142 in the detection area 130. The aggregates include the beads having a detection label, such as the bead 117, and accordingly, the pellet 142 may be detected by detecting the detection label. Aggregates too small to be visually identified individually may still sediment into the pellet and accumulate into a detectable mass, which may result in improved detection capability relative to techniques relying on visual identification of aggregates. An amount of the detection label detected may correspond with an amount of the analyte of interest present in the sample. Because aggregates have formed, no beads or fewer beads are present at the interface between the mixture and the density medium. There may be some labeled beads present at the interface, however, if not all of the labeled beads formed aggregates, such as may be the case if there is a smaller amount of analyte present in the sample.

Referring back to FIG. 1, recall in block 108 the presence of the analyte of interest may be detected and/or quantified. The detection process will vary based, in part, on the detection label used. For example, if a fluorescence label is used, an optical detector may be used to detect the presence of the analyte by detecting the pellet 142 in the detection area 130 of FIG. 2C. If an electronic label is used, an electrical detector, including suitable electrode(s), current and/or voltage supplies and circuitry, may be positioned to detect the electrical detection label in the detection area 130. Other detection modes may also be used. In some examples, the presence of a detection signal generated by a detector may be used to determine the analyte of interest is present in the sample. In some examples, a magnitude or strength of the detection signal may be used to quantify an amount of analyte present in the sample. In some examples, the detection signal from agglutinates may be integrated to quantify the amount of analyte of interest in the sample. In some examples, a volume of the pellet may be measured to quantify the amount of analyte of interest in the sample.

Figure 3:
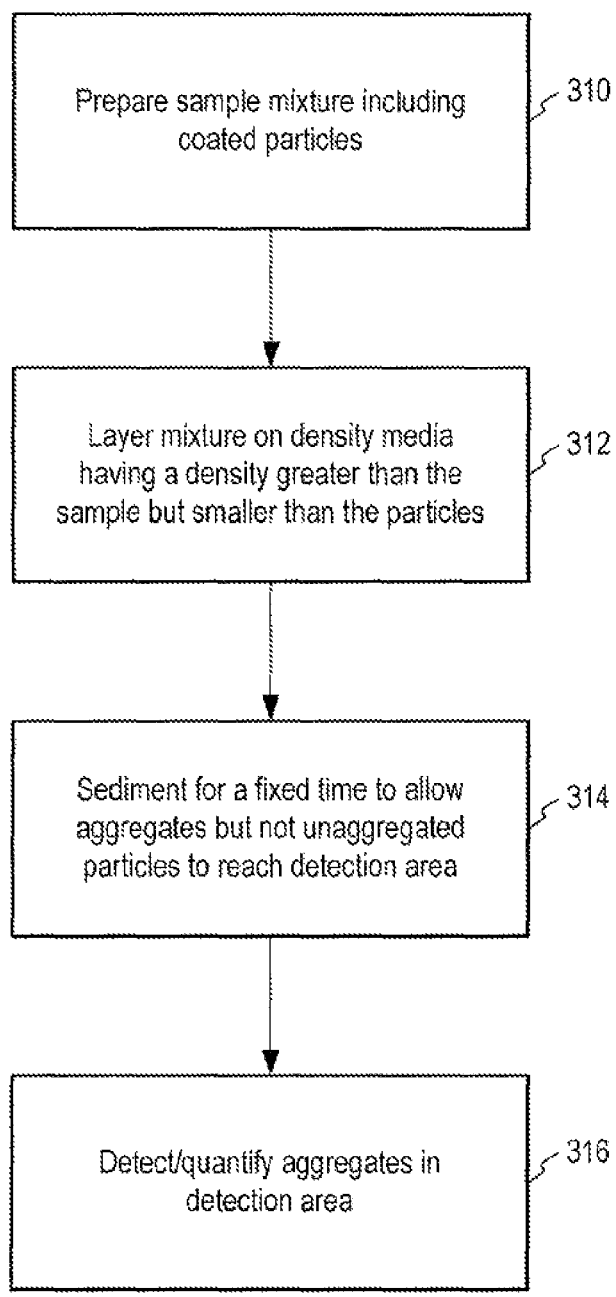
FIG. 3 is a flowchart of another example of a method for conducting an agglutination assay in accordance with embodiments of the present invention.

FIG. 3 is a flowchart of another example of a method for conducting an agglutination assay in accordance with embodiments of the present invention. The method 300 may include in block 310, preparing a mixture including coated particles. The density of coated particles in embodiments in accordance with FIG. 3 may be greater than a density medium used in examples of the invention. In block 312, the mixture may be layered on a density medium having a density greater than the sample but smaller than the particles. Aggregates of analyte and particles may form if analytes of interest are present in the sample. In block 314, the mixture may be subjected to sedimentation forces for a fixed time to allow aggregates, but not unaggregated particles, to reach a detection area. For example, the aggregates are larger than the unbound particles. Accordingly, when subjected to sedimentation forces, the aggregates may travel through the density medium faster than unbound particles. Accordingly, there is a sedimentation time where aggregates will be expected to have arrived at a detection location, but unbound particles would not be expected to arrive at the detection location. Generally, particle sedimentation rate increases with the square of particle size, and this relationship may be used to determine the sedimentation time. In block 316, aggregates may be detected in the detection area. The aggregates may be detected using a label on the particles, such as but not limited to, a fluorescent, electrical, or chemical label as has been described above. In this manner, aggregates too small to be detected visually may also be collected at the detection area and contribute to the detection and/or quantification of the analyte of interest. It is to be understood that additional blocks may be present in some examples. Moreover, aggregates may be formed at any time during the method.

Figure 4:
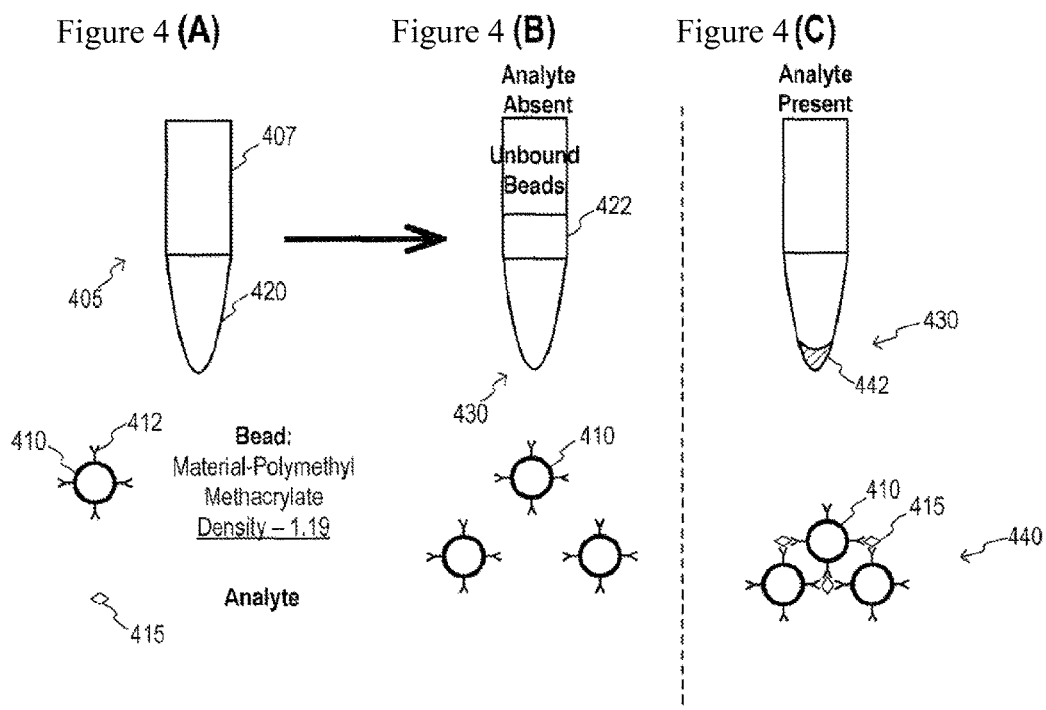
FIGS. 4A, 4B, and 4C are schematic illustrations of different stages of agglutination assays in accordance with embodiments of the present invention.

Example methods arranged in accordance with the flowchart shown in FIG. 3 are further described with reference to FIGS. 4A-4C. FIGS. 4A-4C are schematic illustrations of different stages of agglutination assays in accordance with embodiments of the present invention. The embodiments of the present invention represented in FIGS. 4A-4C may occur during performance of a method according to FIG. 3, e.g. utilize a size-based mechanism for conducting an agglutination assay.

Recall in block 310 of FIG. 3, a mixture may be prepared including a sample and coated particles. The sample may or may not include the analyte of interest. Generally, the particles included in the mixture may have a density greater than the density medium used in the assay. The mixture may be prepared by mixing the particles with the sample, by introducing the sample into a mixture already containing the particles, or through other combinations. In some examples, the mixture is already provided and the block 310 is optional.

FIG. 4A illustrates the mixture 407 contained in a device 405. The device 405 may, for example, be implemented as a vial or a microfluidic device, as will be described further below. The mixture 407 includes a sample and coated particles (e.g. beads). The particles are coated with affinity reagents for the analyte of interest, as has been described above. The example of FIG. 4A illustrates the bead 410 schematically shown below the schematic depiction of the device 405. The bead 410 may have a density greater than the density media. In the example of FIG. 4A, the bead 410 may be implemented as a polystyrene bead having a density of approximately 1.05 g/cm$^2$ and diameter of 1 μm. The bead 410 may be coated with affinity reagents, including the affinity reagent 412, which may be selected to bind with a particular analyte of interest. An analyte of interest 415 is also shown schematically in FIG. 4A. The particles (e.g. beads) may also be labeled with a detection label. As described above, the detection label may include a fluorescent label, chemical label, electronic label, or combinations thereof. As will be described further, detection of the detection label in a detection area may be indicative of the presence of the analyte of interest.

Accordingly, FIG. 4A illustrates a mixture 407 which may include a sample and coated particles including bead 410. The sample may include the analyte of interest 415 or may not. The amount of beads provided in the mixture may vary. Generally, sufficient amounts of beads are provided to generate aggregates for the expected amount of analyte in the sample.

Referring back to FIG. 3, in block 312, the mixture may be layered on a density medium having a density greater than the sample but less than the coated particles. As described with reference to FIG. 4A, the mixture may include particles having a density greater than a density of the density medium. The mixture may be layered on the density medium by providing the mixture in fluid communication with the density medium such that aggregates may pass through the density medium responsive to sedimentation forces. For example, the mixture may be loaded into a device such that the mixture is next to the density medium, on top of the density medium, or separated from the density medium by other fluids or device components.

Referring to FIG. 4A, the mixture 407 is loaded into the device 405 such that it is adjacent the density media 420. For example, if the device 405 is implemented as a vial, the mixture 407 may be pipetted or otherwise dispensed on top of the density medium 420. If the device 405 is implemented as a microfluidic device, the mixture 407 may be introduced to the device next to the density medium 420. In other examples, fluids or device features may separate the density medium 420 and the mixture 407, however, the aggregates may travel across those intervening fluids or features to allow sedimentation of aggregates.

Following block 312 of FIG. 3, in some examples, an incubation period may be provided to allow aggregates to form. In other examples, aggregates may have already formed in the mixture during introduction to a device or prior to introduction to the device. In other examples, aggregates form or continue to form following further blocks of the method. As described above, aggregates may form when the analyte of interest is present in the sample and may not form if the analyte of interest is not present.

Referring back to FIG. 3, in block 314, the mixture may be subjected to sedimentation forces for a fixed time. In some examples, the mixture may be subjected to sedimentation forces using gravity. In other examples, the mixture may be subjected to sedimentation forces using centrifugal forces. The time is selected based on the relative speed of travel of the unbound particles and aggregates through the density medium. The speed of travel will be related to the size of the unbound particles and aggregates, respectively, as well as the density of the density medium and particles. The time selected may also be based on the distance between the sample and the detection area. Generally, the time is selected to allow the aggregates to reach the detection area, but not the unbound particles. Referring to FIG. 4A, in examples where the device 405 is a vial, the vial may be left to incubate in a gravitational field, allowing sedimentation of aggregates, if present, in the mixture 407. Alternatively, the vial may be placed in a centrifuge and the centrifuge spun to allow sedimentation of the aggregates, if present, in the mixture 407.

FIG. 4B is a schematic illustration of the device 405 following exposure to sedimentation forces when no aggregate has formed in the mixture, which may be an indication that no analyte of interest is present in the sample. The lack of aggregate formation is indicated schematically below the device 405 in FIG. 4B. The beads, including bead 410, have not formed aggregates by binding with target analyte, since no analyte or insufficient analyte, is present in the sample. Accordingly, these beads remain unbound in the mixture and travel slowly relative to the speed aggregates would travel through the density medium. Following exposure to sedimentation forces, the particles (e.g. beads) may sediment through the density medium but not reach a detection area because insufficient time was provided for the unbound beads to reach the detection area 430. Accordingly, the beads may be found in an area 422 following sedimentation that may be partially between the initial location of the sample and the detection area 430. However the particles (e.g. beads) may not be found at the detection area. Recall that the beads may include a detection label. Accordingly, the detection label in the example of FIG. 4B may not be found at the detection area 430, and may not contribute to a detection signal measured at the detection area 430.

FIG. 4C is a schematic illustration of the device 405 following exposure to sedimentation forces when aggregate has formed in the mixture, which may be an indication that analyte of interest is present in the sample. The aggregate formation is indicated schematically below the device 405 in FIG. 4C. The beads, including bead 410, may form aggregates, including the aggregate 440. The aggregates are formed in part because the analytes of interest bind to both the bead populations. The analytes of interest, as generally described above, may bind to the beads at respective different sites of the analyte. Accordingly, the analyte 415 of FIG. 4C is shown bound to multiple beads, including the bead 410. The aggregates, including the aggregate 440, are larger than the unbound beads and will accordingly travel faster through the density media 420. Accordingly, following sedimentation, aggregates, including the aggregate 440 may be present in a pellet 442 in the detection area 430. The aggregates include the beads having a detection label, such as the bead 410, and accordingly, the pellet 442 may be detected by detecting the detection label. Aggregates too small to be visually identified individually may still sediment into the pellet and accumulate into a detectable mass, which may result in improved detection capability relative to techniques relying on visual identification of aggregates. An amount of the detection label detected may correspond with an amount of the analyte of interest present in the sample. Any unbound beads will not have reached the detection area 430 due to the fixed time selected for sedimentation, and accordingly unbound beads may not contribute to the detection signal.

Referring back to FIG. 3, recall in block 316 the presence of the analyte of interest may be detected and/or quantified. The detection process will vary based, in part, on the detection label used. For example, if a fluorescence label is used an optical detector may be used to detect the presence of the analyte by detecting the pellet 442 in the detection area 430 of FIG. 4C. The lack of analyte may also be detected by detecting a sufficient amount of label in an area other than the detection area 430, such as by detecting the unbound beads that have not yet reached the detection area 430. If an electronic label is used, an electrical detector, including suitable electrode(s), current and/or voltage supplies and circuitry, may be positioned to detect the electrical detection label in the detection area 430. Other detection modes may also be used. In some examples, the presence of a detection signal generated by a detector may be used to determine the analyte of interest is present in the sample. In some examples, a magnitude or strength of the detection signal may be used to quantify an amount of analyte present in the sample. In some examples, the detection signal from agglutinates may be integrated to quantify the amount of analyte of interest in the sample. In some examples, a volume of the pellet may be measured to quantify the amount of analyte of interest in the sample.

Figure 5:
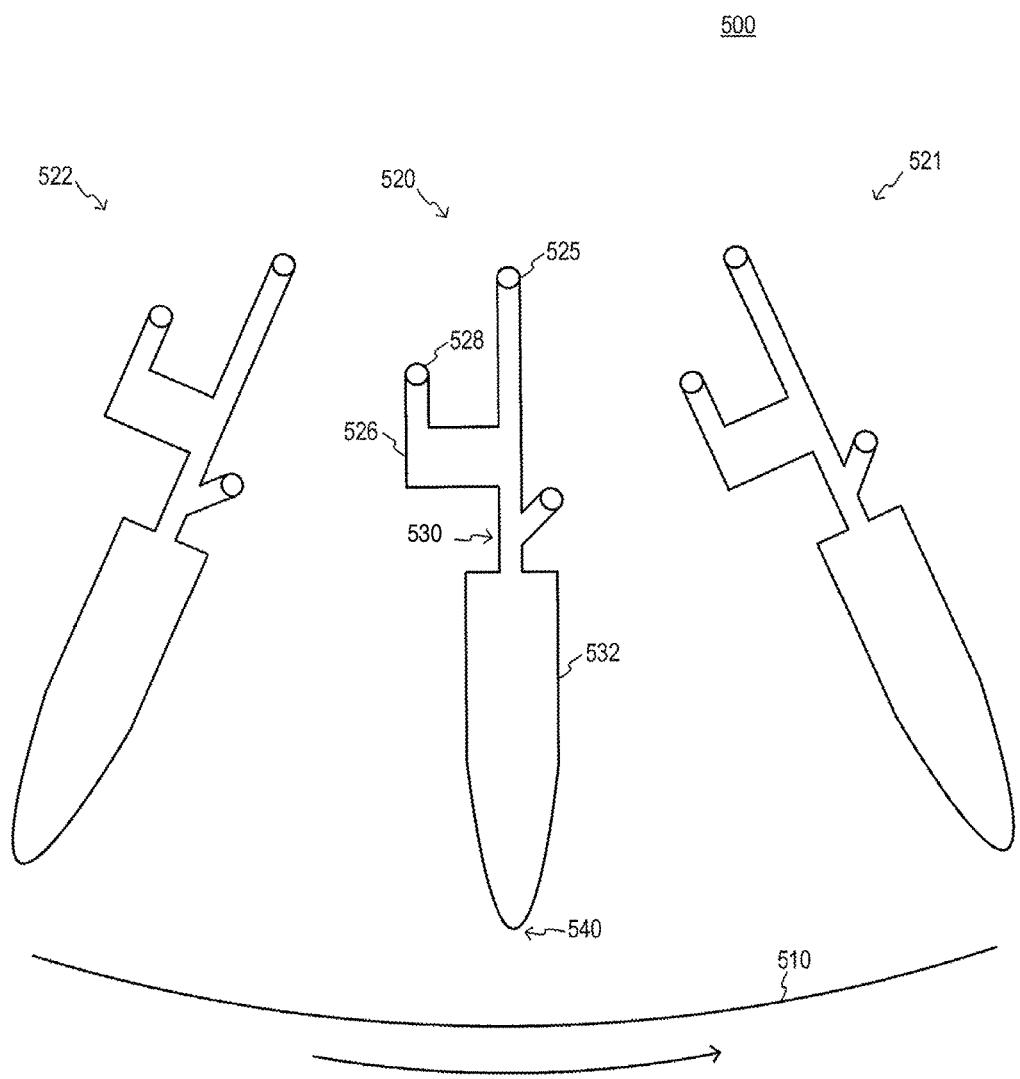
FIG. 5 is a schematic illustration of a microfluidic device arranged in accordance with an embodiment of the present invention.

FIG. 5 is a schematic illustration of a microfluidic device arranged in accordance with an embodiment of the present invention. The device 500 is implemented as a microfluidic disk, however in other examples of the present invention, a disk may not be used and the device 500 may have another form factor. The microfluidic device 500 may include a substrate 510 which may at least partially define regions of assay areas 520, 521, and 522.

The substrate 510 may be implemented using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the device 500. In some embodiments, however, opaque plastic, metal or semiconductor substrates may be used. In some embodiments, multiple materials may be used to implement the substrate 510. The substrate 510 may include surface treatments or other coatings, which may in some embodiments enhance compatibility with fluids placed on or within the substrate 510. In some embodiments surface treatments or other coatings may be provided to control fluid interaction with the substrate 510.

While shown as a round disk in FIG. 5, the substrate 510 may take substantially any shape, including square.

In some embodiments, as will be described further below, the substrate 510 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disc may be disposable. In some examples, a disposable cartridge including one or more microfluidic channels may be inserted into disk or other mechanical rotor that forms part of a detection system.

The substrate 510 may generally, at least partially, define a variety of fluidic features. The fluidic features may be microfluidic features. Generally, microfluidic, as used herein, refers to a system, device, or feature having or including a feature having a dimension of around 1 mm or less and suitable for at least partially containing a fluid. In some embodiments, the microfluidic features may have a dimension of around 100 µm or less. Other dimensions may be used. The substrate 510 may define one or more fluidic features, including any number of channels, chambers, inlet/outlet ports, or other features.

Microscale fabrication techniques, generally known in the art, may be utilized to fabricate the microfluidic device 500. The microscale fabrication techniques employed to fabricate the device 500 may include, for example, embossing, etching, injection molding, surface treatments, photolithography, bonding and other techniques.

Multiple assay areas including assay areas 520, 521, and 522 may be supported by the substrate 510. The multiple assay areas allow multiple assays to be conducted in parallel. For example, a different sample may be introduced to each of the assay areas 520, 521, and 522, and three assays conducted on the assay areas may each include the fluidic features and components for performing an agglutination assay in accordance with examples of the present invention. The features of the assay area 520 are now further described. A fluid inlet port 525 may be provided to receive a fluid that may be analyzed using the microfluidic device 500. The fluid inlet port 525 may have generally any configuration, and a fluid sample may enter the fluid inlet port 525 utilizing substantially any fluid transport mechanism, including pipetting, pumping, or capillary action. The fluid inlet port 525 may take substantially any shape. Generally, the fluid inlet port 525 is in fluid communication with a mixing chamber 526. Generally, by fluid communication it is meant that a fluid may flow from one area to the other, either freely or using one or more transport forces and/or valves, and with or without flowing through intervening structures.

The mixing chamber 526 may be a feature configured to allow for the sample and particles to mix with each other and/or with additional fluids (e.g. buffers, reagents, etc.). Another fluid inlet port 528 may be in fluid communication with the mixing chamber 526 for the introduction of coated particles or other species into the mixing chamber 526. Accordingly, during operation, sample fluid may be introduced to the mixing chamber 526 through the fluid inlet port 525 and coated particles, which may be suspended in a buffer or other fluid, may be introduced to the mixing chamber 526 through the inlet port 528, or may already be present in the mixing chamber 526. It is to be understood that the form factor and layout of the microfluidic components described herein is quite flexible, and for example, the mixing chamber 526 may take substantially any form factor including a chamber, reservoir, or channel. The mixing chamber 526 generally refers to a portion of the microfluidic device 500 suitable for holding sample fluid and coated particles. A mixer may be included in some embodiments to mix fluids contained in the mixing chamber 526.

A valve 530 is provided for fluidic separation between the mixing chamber 526 and reservoir 532. The valve 530 may be used to contain fluids in the mixing chamber 526 for a period of time to allow the fluids to mix (e.g. sample and coated particles), and may then be opened to allow the mixture into the reservoir 532. Any suitable valve may be used, including but not limited to a wax valve.

The reservoir 532 may generally be implemented using any size and shape, and may contain one or more reagents including solids and/or fluids which may interact with fluid entering and/or exiting the features. The reservoir 532 may be implemented as the device 405 of FIG. 4 or the device 205 of FIG. 2. The reservoir 532 may be configured to contain a density medium and receive a mixture containing the sample and coated particles. The substrate 510 may spin, for example in a direction indicated by the arrow in FIG. 5 (or in the opposite direction in other examples), and the spinning of the substrate may generate a centrifugal force which may provide the sedimentation forces described above to move unbound beads and/or agglutinate toward a detection area 540.

The detection area 530 may be a channel or chamber, or a location within a particular feature, such as an end of the reservoir 532 in FIG. 5, and may vary in configuration in accordance with the detection technique employed. The detection area 530 may generally be configured to allow for detection of a signal emitted by labels on coated particles or unbound particles and/or aggregates.

Figure 6:
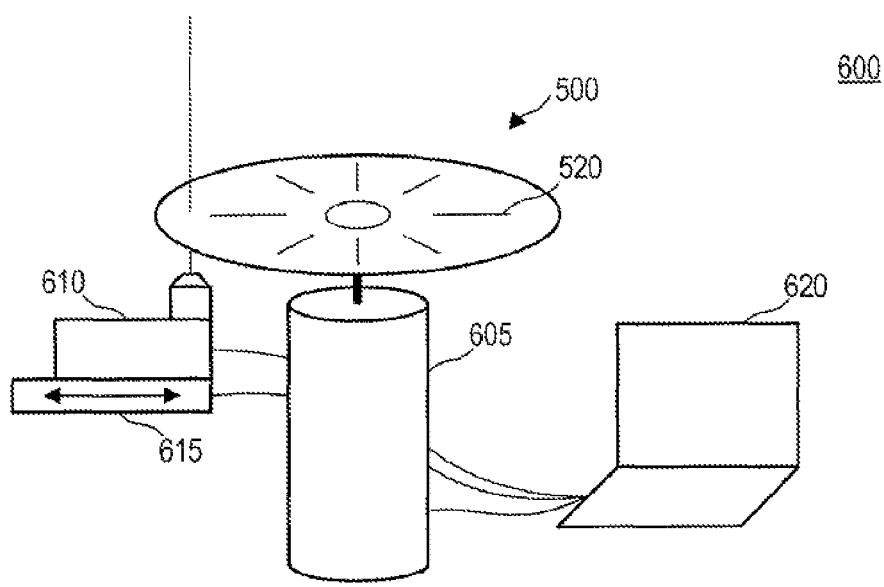
FIG. 6 is a schematic illustration of a system according to an embodiment of the present invention.

FIG. 6 is a schematic illustration of a system according to an embodiment of the present invention. The system 600 may include the device 500 of FIG. 5 with one or more assay areas 520. A motor 605 may be coupled to the device 500 and configured to spin the device 500, generating centrifugal forces. A detection module 610 may be positioned to detect signal from labels in a detection region of the assay area 520, as will be described further below. An actuator 615 may be coupled to the detection module 610 and configured to move the detection module along the detection region in some examples. A processing device 620, e.g. a computer, controller, or the like, may be coupled to the motor 605, the detection module 610, and/or the actuator 615 and may provide control signals to those components. The processing device 620 may further receive electronic signals from the detection module 610 corresponding to the label signals received by the detection module 610. The processing device 620 may allow for automated control of the motor 605 and detection module 610 such that multiple parallel assays on the device 500 may be automated. All or selected components shown in FIG. 6 may be housed in a common housing in some examples. Microfluidic disks, which may be disposable, may be placed on the motor 605 and removed, such that multiple disks may be analyzed by the system 600.

The motor 605 may be implemented using a centrifugation and/or stepper motor. The motor 605 may be positioned relative to the detection module 610 such that, when the device 500 is situated on the motor 605, the disk is positioned such that a detection region of the assay area 520 is exposed to the detection module 610.

The detection module 610 may include a detector suitable for detecting signal from labels on the coated particles described herein. The detector may include, for example, a laser and optics suitable for optical detection of fluorescence from fluorescent labels. The detection module may include one or more photomultiplier tubes. In other examples, other detectors, such as electronic detectors, CCD cameras, or other cameras (e.g. cell phone cameras), may be used. The actuator 615 may move the detector in some examples where signal may be detected from a variety of locations of the microfluidic device 500, as will be described further below.

The processing device 620 may include one or more processing units, such as one or more processors. In some examples, the processing device 620 may include a controller, logic circuitry, and/or software for performing functionalities described herein. The processing device 620 may be coupled to one or more memories, input devices, and/or output devices including, but not limited to, disk drives, keyboards, mice, and displays. The processing device may provide control signals to the motor 605 to rotate the device 500 at selected speeds for selected times, as has been described above. The processing device may provide control signals to the detection module 610, including one or more detectors and/or actuators, to detect signals from the labels and/or move the detector to particular locations. The processing device may develop these control signals in accordance with input from an operator and/or in accordance with software including instructions encoded in one or more memories, where the instructions, when executed by one or more processing units, may cause the processing device to output a predetermined sequence of control signals. The processing device 620 may receive electronic signals from the detection module 610 indicative of the detected signal from labels. The processing device 620 may detect an analyte of interest and/or calculate a quantity of a target analyte in a fluid sample based on the signals received from the detection module 610, as has been described above. Accordingly, the processing device 620 may perform calculations. The calculations may be performed in accordance with software including one or more executable instructions stored on a memory causing the processing device to perform the calculations. Results may be stored in memory, communicated over a network, and/or displayed. It is to be understood that the configuration of the processing device 620 and related components is quite flexible, and any of a variety of computing systems may be used including server systems, desktops, laptops, controllers, and the like.

From the foregoing it will be appreciated that, although specific embodiments of the invention have been described herein for purposes of illustration, various modifications may be made without deviating from the spirit and scope of the invention.

What is claimed is:

1. A microfluidic device for conducting an agglutination assay, the microfluidic device comprising:
    a substrate at least partially defining or supporting:
        a mixing chamber comprising a mixture, wherein the mixture includes a sample and a population of coated particles having a density, wherein the population of coated particles include affinity reagents for an analyte of interest, wherein the population of coated particles forms aggregates with the analyte of interest when present in the mixture;
        a reservoir containing a density medium, wherein the density medium has a minimum density that is greater than the density of the coated particles;
    wherein the mixing chamber and the reservoir are in fluid communication with each other such that the mixture becomes layered on the density medium in the reservoir, and further wherein the aggregates, if formed, travel through the density medium in the reservoir responsive to sedimentation forces.

2. The microfluidic device of claim 1, wherein the substrate comprises a disk configured to rotate to generate the sedimentation forces.

3. The microfluidic device of claim 1, wherein the affinity reagents bind the analyte of interest at multiple locations.

4. The microfluidic device of claim 1, further comprising a valve between the mixing chamber and the reservoir.

5. The microfluidic device of claim 1, further comprising a detection area in fluid communication with the reservoir, wherein the aggregates, if formed, are collected in the detection area responsive to the sedimentation forces.

6. The microfluidic device of claim 1, wherein the substrate at least partially defines a plurality of assay areas for conducting parallel assays.

* * * * *